United States Patent

Sims

[11] Patent Number: 5,340,384
[45] Date of Patent: Aug. 23, 1994

[54] VACUUM DEGASSING

[75] Inventor: Carl W. Sims, St. Paul, Minn.

[73] Assignee: Systec, Inc., Minneapolis, Minn.

[21] Appl. No.: 26,730

[22] Filed: Mar. 5, 1993

[51] Int. Cl.$^5$ .................... B01D 19/00; B01D 63/06
[52] U.S. Cl. ............................................. 96/6; 96/10; 96/193
[58] Field of Search ............... 95/46, 248, 266; 96/6, 96/10, 193, 194

[56] References Cited

U.S. PATENT DOCUMENTS

| | | | |
|---|---|---|---|
| 3,303,105 | 2/1967 | Konikoff et al. | 55/16 X |
| 3,367,850 | 2/1968 | Johnson | 55/16 X |
| 3,437,357 | 4/1969 | Rubin | 55/158 X |
| 3,463,615 | 8/1969 | Sochor | 55/36 X |
| 3,469,369 | 9/1969 | Helmke | 55/46 |
| 3,640,822 | 2/1972 | Hrdina | 55/55 X |
| 3,651,616 | 3/1972 | Blanchard et al. | 55/16 |
| 3,662,520 | 5/1972 | Saunders | 96/10 |
| 3,665,680 | 5/1972 | Heuser | 96/10 |
| 3,668,837 | 6/1972 | Gross | 55/158 |
| 3,678,654 | 7/1972 | Low et al. | 55/16 |
| 3,730,351 | 5/1973 | Veronesi | 210/321 |
| 3,751,879 | 8/1973 | Allington | 55/158 |
| 3,856,475 | 12/1974 | Marx | 55/16 X |
| 3,880,759 | 4/1975 | Van Assendelft | 210/194 |
| 3,972,695 | 8/1976 | Buckley et al. | 55/158 |
| 4,056,373 | 11/1977 | Rubin | 55/158 |
| 4,133,767 | 1/1979 | Bakalyar et al. | 55/47 X |
| 4,325,715 | 4/1982 | Bowman et al. | 55/158 |
| 4,366,700 | 1/1983 | Bouck | 96/6 X |
| 4,430,098 | 2/1984 | Bowman et al. | 55/191 |
| 4,469,495 | 9/1984 | Hiraizumi et al. | 55/189 |
| 4,629,561 | 12/1986 | Shirato et al. | 210/198.2 |
| 4,729,773 | 3/1988 | Shirato et al. | 55/158 |
| 4,787,921 | 11/1988 | Shibata et al. | 96/6 |
| 4,902,419 | 2/1990 | Shibata et al. | 96/6 X |
| 4,985,055 | 1/1991 | Thorne et al. | 96/6 |
| 4,986,837 | 1/1991 | Shibata | 96/6 |
| 4,994,180 | 2/1991 | Sims et al. | 210/198.2 |
| 4,997,464 | 3/1991 | Kopf | 96/6 |
| 5,019,140 | 5/1991 | Bowser et al. | 96/6 |
| 5,100,555 | 3/1992 | Matson | 95/46 X |
| 5,183,486 | 2/1993 | Gatten et al. | 55/159 |

FOREIGN PATENT DOCUMENTS 2658285 10/1977 Fed. Rep. of Germany.
2907188 8/1979 Fed. Rep. of Germany.
1213836 4/1960 France.

Primary Examiner—Robert Spitzer
Attorney, Agent, or Firm—Haugen and Nikolai

[57] ABSTRACT

A flow-through vacuum degassing unit for degassing a liquid includes a vacuum chamber adapted to be connected to a source for creating a vacuum in the chamber, inlet and outlet connections for admitting and discharging liquid to be degassed and one or more tubes for conducting the liquid through the chamber, wherein the tube is formed in a predetermined, memoried configuration and capable of self-supported containment in the vacuum chamber, the tube being of a thin-walled semi-permeable polymeric resin material.

18 Claims, 3 Drawing Sheets

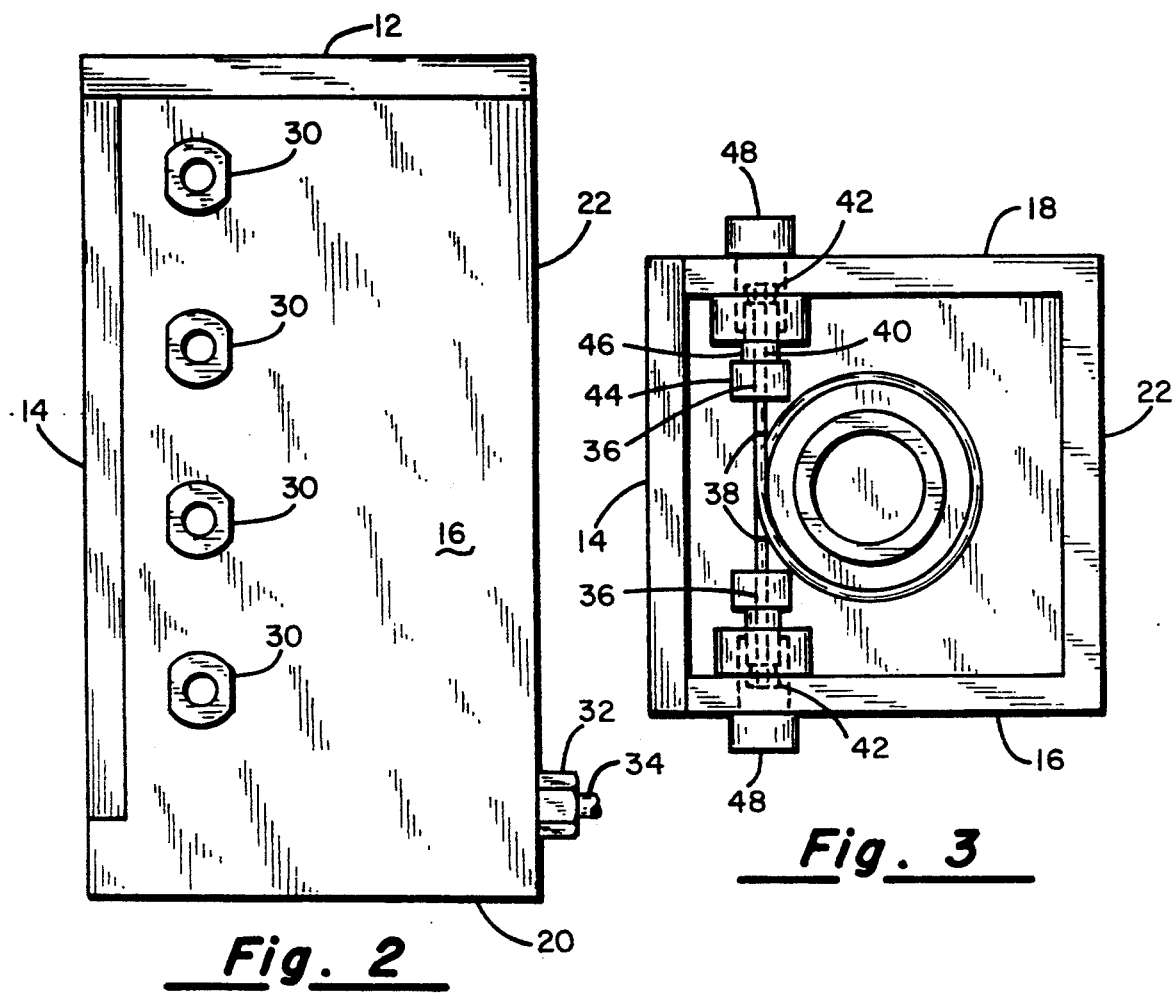
Fig. 2
Fig. 3
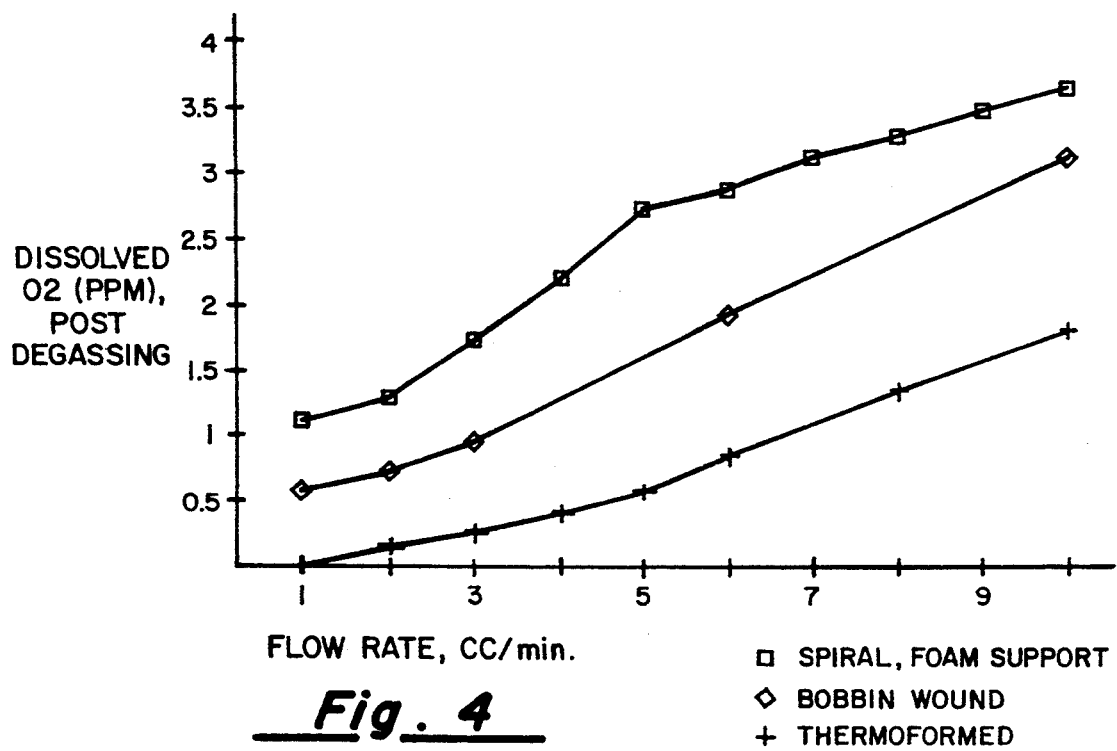
Fig. 4
□ SPIRAL, FOAM SUPPORT
◇ BOBBIN WOUND
+ THERMOFORMED

VACUUM DEGASSING

BACKGROUND OF THE INVENTION

I. Field of the Invention

The present invention is directed generally to the field of vacuum degassing of liquids and, more particularly, to a method and apparatus associated with removing gases from liquids in a flow-through relation in which an elongated semi-permeable polymeric resin enclosure addresses a vacuum chamber and gas is transferred by diffusion through the enclosure walls. The technique is particularly suited to the removal of air or oxygen from solvent materials associated with liquid chromatograph equipment.

II. Related Art

There are many chemical applications, particularly analytical applications, involving the use of liquid solvents, reactants or the like in which the presence of dissolved gases, particularly air, is undesirable. A prime example of such a situation relates to solvents and chemicals used in liquid chromatography where the presence of even small bubbles of dissolved gases typically interferes with the accuracy and sensitivity of the results obtained. If the dissolved species be chemically active, as is the case with oxygen in air, it can additionally produce unwanted changes or deterioration of the liquid material of interest. Of course, the detrimental effect of the dissolved species is related to the relative concentration of the species in the liquid. These undesirable species usually are removed by a degassing process. It correspondingly follows that the more efficient the removal or degassing system is, the more desirable it will be.

The degassing of liquid materials has been necessary to the success of many processes and, consequently, the process has been pursued actively in several forms for a long period of time. Techniques have included heating or boiling the liquid, exposing the material to a reduced pressure environment or vacuum and using combinations of heat and vacuum to reduce the amount of dissolved gases in the liquid. Ultrasonic energy has also been employed. As conventionally applied, however, these traditional techniques have generally fallen short of the desired degree of separation efficiency. Additionally, a means of degassing solvent involving the passing of a fine stream of bubbles of inert gas such as helium through the solution to be degassed has been shown by Bakalyar et al in U.S. Pat. No. 4,133,767, and in apparatus such as that disclosed by Sims et al in U.S. Pat. No. 4,994,180, co-invented by the inventor in the present application and assigned to the same assignee as the present invention. Helium degassing has been established as the standard for thoroughly removing dissolved gases such as oxygen, nitrogen and other similar components of the atmosphere. Helium sparging for the purpose of degassing, however, has drawbacks such as selectively removing important volatile components of mixed solvents, and requiring large tanks for the supply of helium. Vacuum degassing through a membrane apparatus has been long known, and generally utilizes a membrane permeable only to fixed gases. Degassing by this means is generally established as being capable of reaching 0 concentration of atmospheric gases, and leaves only minor amounts of Helium dissolved in the solvent. For comparison purposes, all tests involved in demonstrating the present invention were run versus Helium degassing as a baseline.

A more recent approach to degassing relatively small volumes of materials involves the provision of the length of relatively small diameter, thin-walled semipermeable synthetic polymer resin tube contained within an enclosed chamber held under a reduced pressure or vacuum in which the liquid to be degassified is caused to flow through the tube. Amounts of the dissolved gas diffuse through the wall of the tube according to the pressure reduction, permeability, time and area exposed and temperature. These tubes tend to collapse and kink easily, and so must be carefully configured and supported.

Examples of devices of this type include devices such as that illustrated and described in U.S. Pat. No. 5,183,486, in which the tubes exposed within the vacuum chamber conveying the liquid to be degassed are wound in tension on bobbins or spools which support and maintain the inter-coil separation of the rather thin, fragile tubes. Another degassing apparatus is disclosed is U.S. Pat. No. 4,469,495, which employs a coil of semi-permeable polymer resin material containing a plurality of turns. The coil is also quite prone to collapse or kinking and so is required to be supported and the turns separated by a plurality of spacer elements which prevent such physical problems but, unfortunately, in turn, mask a large portion of the area which otherwise could be exposed to the vacuum. Other configurations are shown in U.S. Pat. Nos. 4,430,098, 4,325,715, 3,668,837 and German Offenlegungsschrift 29 07 188.

While each of these devices employs a flow-through tube vacuum degassing approach, and each of the devices has been at least somewhat successful, there remains a need, particularly with devices associated with liquid chromatograph instruments, to make degassing of chemicals and solvents more efficient. One particular limitation or drawback associated with present devices concerns the efficiency of the degassification operation with respect to the tubing itself. Because the tubing must be thin walled to aid diffusion, it tends to collapse and kink readily. In order to overcome these physical limitations, much of the tubing wall surface is masked from the vacuum by apparatus to support and preserve the tubing shape to prevent flow problems. This surface area is lost with respect to the diffusivity. In addition, the efficiency could be further increased if this problem could be overcome and the required wall thickness could be decreased even more.

Accordingly, it is a principal object of the present invention to provide a more efficient liquid vacuum degassing system of the flow-through type using a semipermeable resin tube that maximizes exposed tubing surface and minimizes required wall thickness.

A further object of the present invention is the provision of a form-memoried, self-supporting helical tube for a flow-through vacuum degassing unit.

A still further object of the present invention is to provide a coiled tube vacuum degassing system which maximizes the exposed tube area by eliminating the need for tube supports and coil turn spacers, thereby minimizing the effect of unusable wall contact areas.

A yet further object of the present invention is to provide a semi-permeable flow-through coil vacuum degassing system that reduces the length of tubing required in the degassing operation.

Another object of the present invention is to reduce the elapsed time to the point the degassified solvent or chemical is available at the output of the device of a semi-permeable flow-through coiled tube vacuum degassing device.

Still another object of the invention is to provide an improved connection system for a synthetic resin semi-permeable tube associated with a flow-through vacuum degassing apparatus.

A still further object of the invention is to reduce the required wall thickness of the tube in a flow-through semi-permeable coiled tube vacuum degassing system.

SUMMARY OF THE INVENTION

By means of the present invention, the efficiency of a flow-through vacuum degassing system utilizing an elongated semipermeable polymeric resin tube degassing interface is improved by eliminating the need for inter-turn spacer elements or coiled tube supports, thereby maximizing the surface area exposure of the elongated resin tube to the vacuum. Inasmuch as the coiled tube of the present invention requires no special support and also maintains its cylindrical cross-section configuration, the contact area between coils or between a coil and the adjacent surface is minimized or reduced to line contact. The tube coil is preferably draped about an inside spool which functions as a guide means rather than as a tube support.

According to the present invention, it has been discovered that certain semi-permeable polymeric resin tubing materials may be thermally treated in a manner that improves the qualities required for use in vacuum degassing systems of the class described. The tubing used in the vacuum degassing system of the present invention is preferably thermally formed into a memoried helical coil by winding the tubing on a mandrel of the desired size which is thereafter heated in an oven. The tubing is heated to an elevated temperature, usually 350° to 400° F. (175° to 205° C.). The tube is inflated to an elevated pressure for a specified period of time, typically 20 PSIG (1.4 Kg/cm$^2$) for a 0.04 mm thick tube. The oven heat is then removed and the tubing is maintained in an inflated condition to preserve its cylindrical cross-sectional shape while the tubing, while still on the mandrel, is thereafter allowed to cool back down to room temperature. This process produces a memoried helical coil of semi-permeable synthetic polymer resin tubing having a relaxed shape optimized to fit the inside dimension of the vacuum chamber and one which resists kinking and other undesirable conditions of an unsupported tube coil.

The preferred material for the tube is polytetrafluoroethylene (PTFE), although other materials having the requisite properties can be used, such as fluorinated ethylene propylene (FEP), PFA or other fluorinated polymers, and the heat processing further allows the use of ultra thin-wall extruded tubing, i.e., as thin as extrusion techniques permit, presently allowing a wall thickness as thin as 0.013 mm and generally one in a range of 0.013 mm to 0.04 mm. This may be compared with wall thicknesses in prior art devices in the range of 0.2 mm to 1.0 mm. This represents an available reduction in wall thickness greater than a full order of magnitude; and since degassing efficiency is directly related to the thickness of the gas permeable membrane, degassing performance is greatly enhanced by the design of the present invention.

This greatly improved permeability allows the length of tube within the vacuum degassing chamber to be greatly decreased for the same quantitative degassing result. In accordance with one embodiment, a system under 700 mm Hg vacuum utilizing 25 feet (7.62 M), of 0.064 inch internal diameter (1.6 mm) has been used to degassify reagent grade water saturated with air to 0.1 PPM oxygen at a throughput or flow rate of 1 ml/min. In this manner, the present invention provides a device for removing dissolved gases using an elongated flow-through tube which is able to utilize the thinnest available tube wall by heat treating it to provide a stable, thermally formed, self-supporting tube coil for use in the vacuum. It has been found that not only does the treated tubing resist kinking, it also readily retains its desirable cylindrical shape, and this property is, of course, enhanced when the tubing is exposed to a vacuum.

An additional feature of the present invention deals with the elimination of metal to solvent or chemical contact with respect to the material of interest to be degassed. The preferred vacuum chamber in accordance with the present invention is fabricated entirely from high-impact polymers such as polyethylene or polypropylene, which is preferably welded together but may be assembled using appropriate high-strength adhesives. The tube connections which hold the inlet and outlet ends of the degassing tube may be made metal-free with respect to those parts that come in contact with the solvent or the chemical being degassed.

The degassing chamber of the invention includes a high-impact chemically benign housing provided with inlet and outlet connections for one or more coils of semi-permeable polymer resin tubing, together with an optional guiding spool means to retain the one or more coils in an approximate desired position and connection means for connecting a vacuum pump and gauge system to the housing.

BRIEF DESCRIPTION OF THE DRAWINGS

In the drawings, wherein like numerals designate like parts throughout the same:

FIG. 2 is a side view of the vacuum chamber of FIG. 1;

FIG. 3 is a top view of the vacuum chamber of FIG. 1 with the top plate removed;

FIG. 4 is a comparative graph showing relative degassing efficiency of several types of semi-permeable synthetic resin tube configurations.

DETAILED DESCRIPTION

Figure 1:
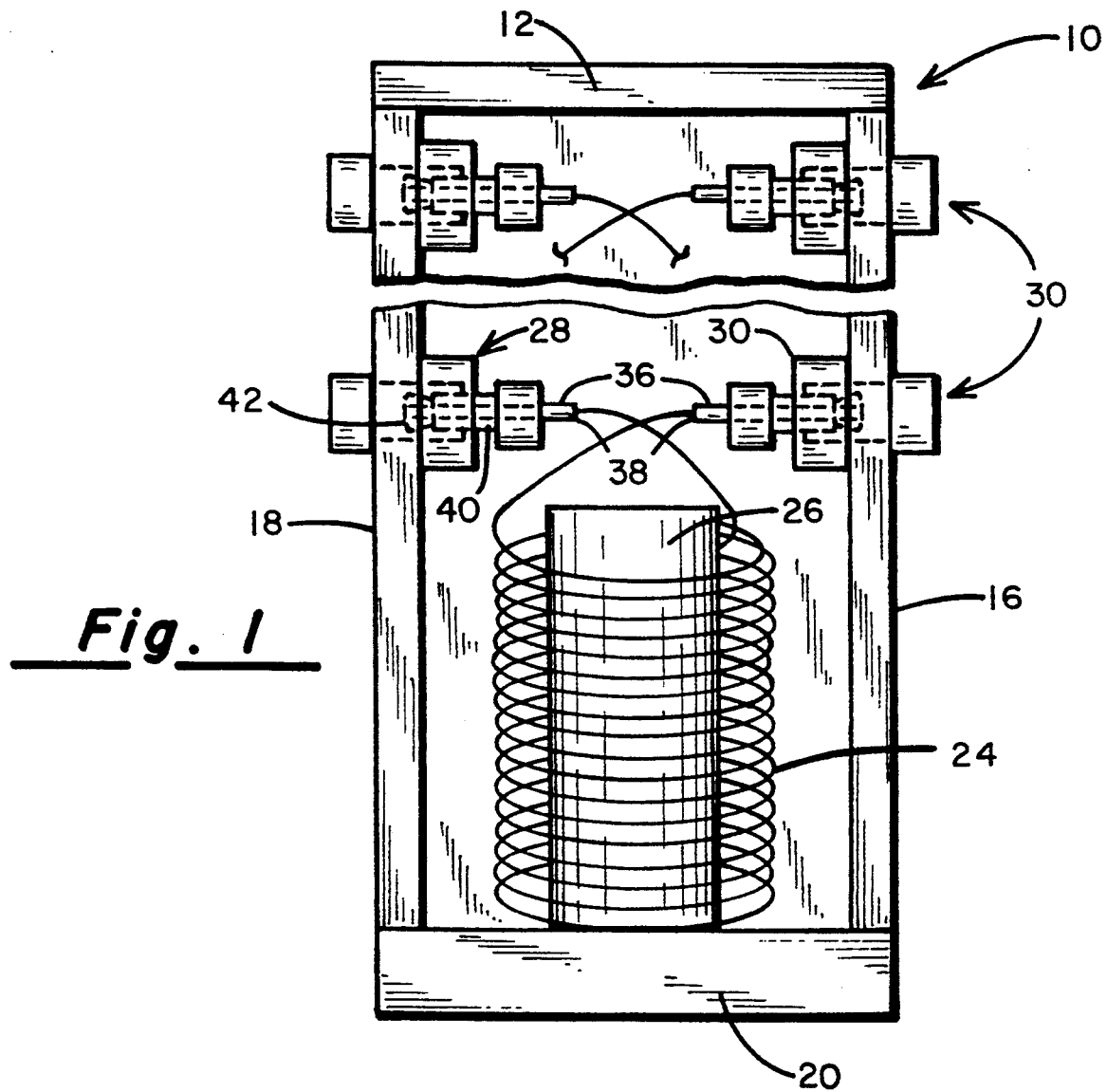
FIG. 1 is an internal view of a typical vacuum chamber in accordance with the invention for use with a multiple number of coils shown with parts broken away.

The objects and advantages enumerated above together with other objects, features and advances represented by the present invention will now be presented in terms of a detailed embodiment described with reference to the attached drawing Figures which are intended to be but representative of many possible configurations of the invention. Other embodiments and aspects of the invention are recognized as being within the grasp of those having ordinary skill in the art. With particular initial reference to FIGS. 1-3, there is shown generally at 10 a vacuum degassing chamber having a top member 12, a front wall member 14 (FIG. 2) and a housing having sides 16 and 18 (FIG. 1) and bottom 20 with a rear wall 22.

The housing itself forming the vacuum chamber is preferably made of high-impact polymer material, such as high-density polyethylene or polypropylene, which can be readily heat welded together to form a strong, relatively inert, non-metallic housing or shell. A typical degassing tube is shown schematically at 24 as being loosely constrained by a central shaft or spool member 26 and connected between inlet and outlet connections 28 and 30. Additional coils can be similarly contained within the chamber 10 as shown in the broken away top portion of FIG. 1 and with the additional connector systems 28 and 30 (FIGS. 1 and 2). The housing further contains, as shown in FIG. 2, a connection as at 32 for a vacuum line 34, which is designed to be connected in a well-known manner to a vacuum pump (not shown) which forms the part of a larger system well-known to those skilled in the art and which additional elements form no part of the present invention.

Figure 5A:
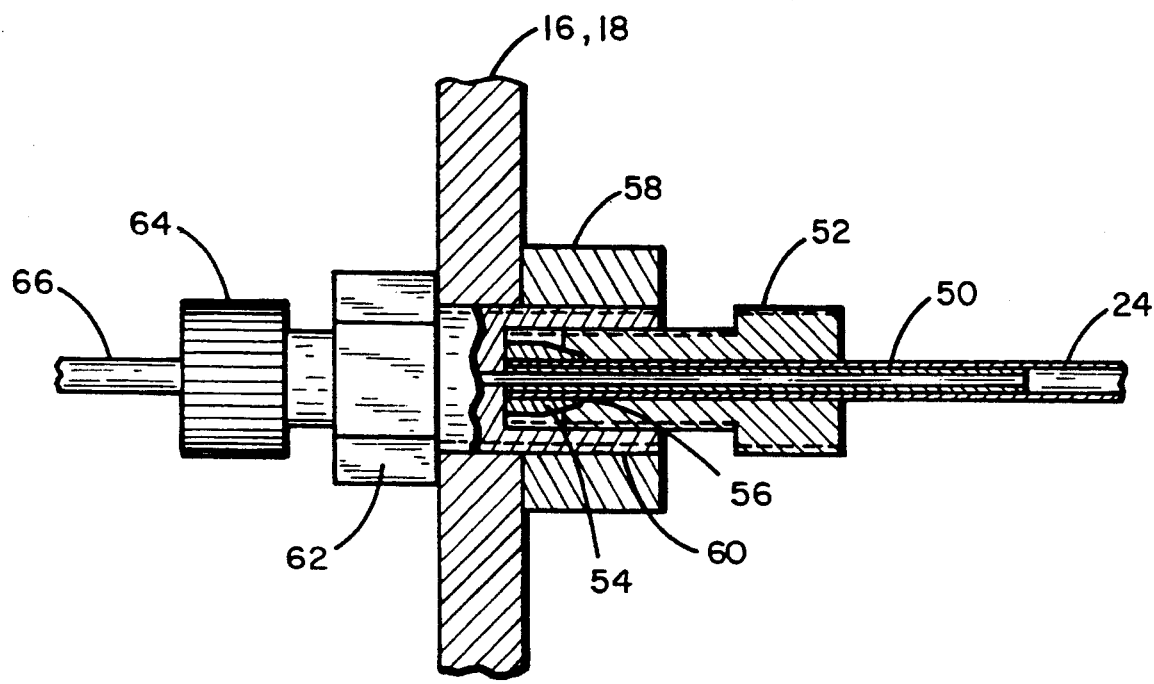
FIGS. 5A and 5B are greatly enlarged views, partially in section, of alternate inlet/outlet connections configured in accordance with the invention.
Figure 5B:
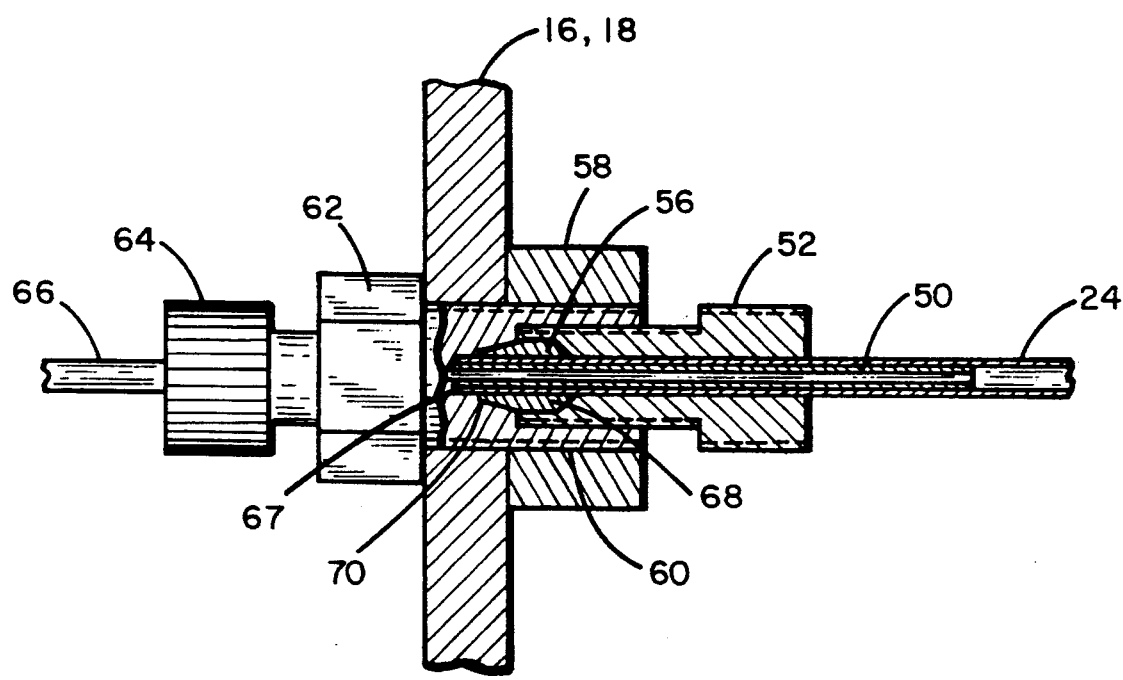

In accordance with one important aspect of the present invention, the connections as at 28 and 30, the parts of which are shown in greater detail in the greatly enlarged views of FIGS. 5A and 5B, as shown generally in FIGS. 1 and 3, include a short length of tubing 36 which may be high strength, high density, relatively inert material, such as poly ether ether ketone (PEEK) or, if metal, titanium, for liquid chromatography solvents and having an end as at 38 over which the corresponding end of the degassing tube coil 24 is fitted. This tube member is typically 0.0625 inch OD (0.16 cm) and about 0.050 inch ID (0.127 cm) and extends into the connection as shown by the dotted lines in FIGS. 1 and 3 at 40. The tube is further connected using an appropriate sealing ferrule 42 which may be of tefzel or other high-impact inert material used in conjunction with a hex nut 44 to connect to the fitting 46. The outer fitting 48 is typically of poly ether ether ketone (PEEK). Details of specific embodiments appear in FIGS. 5A and 5B discussed below. In this manner, the entire tube connection may be made metal-free.

FIGS. 5A and 5B illustrate greatly enlarged views, partially in section, of alternate tubing connection systems with reference to a vacuum tube inlet or outlet connection for a typical tube 24. The materials of construction can be any suitable materials commensurate with the materials to be handled and degree of sealing necessary. Thus, for example, for use with liquid chromatograph solvents and chemicals, materials can be 300 series stainless steel, e.g., 316 stainless steel, titanium, polymeric materials such as poly ether ether ketone (PEEK) or any other chemically inert material.

The degassing tube 24 is stretched or just fits over a liner tube 50 and both are inserted into the fitting or connector system and held in place by a reverse ferrule nut 52 formed to provide a sealing interface 56 with reverse ferrule 54 squeezing the tubing 24 against the liner tube 50 to provide a liquid-tight seal. A bulkhead connector nut 58 is threadably attached at 60 to sidewall or bulkhead 16, 18. The conventional outer sealed connection includes an outer wall or bulkhead union 62 suitably sealed to maintain vacuum at threads 60 is provided together with inlet/outlet outer connecting compression nut 64 which seals the connection of tube 66 with a conventional internal ferrule (not shown).

The connection system of FIG. 5B is similar to that shown in FIG. 5A, except that the tubes 24 and 50 are extended into the wall or bulkhead 16, 18 at 67 and sealed using a double sealing ferrule 68 adding additional sealing interface 70 close to the end of the tubes 24, 50.

In accordance with an important aspect of the invention, the tubing coil 24 is heat treated to establish or reestablish a thermally formed memoried coil shape of substantially round cross-section. Thus, in accordance with the present invention, it has been found that a thermal treatment of extremely thin-walled polytetrafluoroethylene (PTFE), fluorinated ethylene propylene (FEP) or similarly reacting semi-permeable tubing can reestablish a memory in that tubing in the form desired for use in the vacuum chamber which renders the tubing in the memoried configuration substantially self-supporting and eliminates the need for any external means to sustain the shape of either the tubing itself as a continuous open cylinder, i.e., preventing kinking of the tubing or the coil itself or the shape of the multi-turn coil itself. It is anticipated that such a heating process could be useful to produce other shapes and for other applications of such tubing or the like also.

Prior to use in the vacuum degassing chamber, the tubing used in the present invention is thermally formed into a helical coil by winding it upon a mandrel of the desired diameter and heating the wound mandrel in an oven or other chamber of controlled temperature. The tubing is generally heated to an elevated temperature, usually in the vicinity of 350° to 400° F. (175° to 205° C.). The tube is thereafter inflated to an elevated pressure and held at temperature for a specific period of time to establish the helical and cylindrical, open tube configuration. The pressure utilized, of course, depends at least in part on the relative tubing size and wall thickness. For example, an ultra thin-wall extruded PTFE tube having a wall thickness as thin as 0.13 mm, the typical internal diameter of 1.6 mm is normally inflated to a pressure of about 20 PSIG (1.4 Kg/cm$^2$). The only constraints on pressurizing the tube involves exceeding the elastic limit of a particular thickness of the tube at the elevated temperature. After being held at that temperature and pressure for a specified time, which depends on the precise application, the mandrel containing the tubing is then allowed to cool to ambient or room temperature still in the inflated condition.

It has been found that this process produces a memoried helical coil with the ability to maintain both the general shape of the helix and the round openness with respect to the tubing itself with sufficient integrity such that no external means are required to maintain the integrity of the helical coil within the vacuum chamber, once attached to the tubular fittings. The member 26 is optionally provided as a guide to the placement of the coil in the chamber but is by no means necessary to sustain the coil once attached.

In this manner, in accordance with the present invention, ultra thin-wall extruded PTFE tubing having a wall thickness as thin as 0.13 mm and generally in a range of 0.13 mm to 0.04 mm has been successfully utilized in vacuum degassing apparatus. This may be compared to prior art wall thicknesses in the range of 0.2 mm to 1.0 mm and represents a reduction in wall thickness greater than a full order of magnitude in a coil having a much greater working stability than the existing thicker-walled tubing coils.

As is well known in the gas diffusion art, the permeability of and, hence the diffusion of, a species through a semi-permeable membrane is directly related to the thickness of that membrane. This means that a degassing diffusion rate of the tubing utilized in the vacuum degassing chamber of the present invention provides an improvement in efficiency of at least an order of magnitude from that reported in the literature.

Not only does the freestanding thermally formed helical coil allow the use of much thinner tubing wall structures, it also eliminates the reduction in area directly exposed to the chamber vacuum associated with such devices as foamed supports and spacers or bobbins against which the tubing is wound under tension for support. Both of these techniques, of course, either mask or flatten substantial portions of the tubing area, thereby reducing the area for gas outflow along the length of the tube.

FIG. 4 shows a comparison of three well-known vacuum degassing semi-permeable polymer resin tube systems with respect to degassing efficiency. The comparison is based on data taken utilizing three vacuum degassing units, two of which are commercially available units, and the third utilizing the thermal formed degassing coil of the invention. As seen in FIG. 4, the curve utilizing the square designation represents a foam supported spiral coil having inter-coil spacers as manufactured by Erma Optical Works, Ltd. of Tokyo, Japan; the coil using the diamond designation represents a bobbin-wound tensioned system manufactured by Showa Denko KK Specialty Chemicals Division, Shodex Separation & HPLC Group of Tokyo, Japan, or Spectra Physics, Inc. of San Jose, Calif., and the curve designated by the "+" signs represents a vacuum degassing unit in accordance with the present invention utilizing a 0.064 inch ID (1.6 mm) tube having a wall thickness of 0.0015 inch (0.38 mm). The liquid used is atmosphere saturated water at approximately 25° C. As can be seen from the Figure, the vacuum degassing apparatus of the present invention consistently outperforms the other units at any flow rate. This is accomplished using a tube having a wall which is only one-third as thick as the minimum wall thickness that has been successfully utilized previously. Thus, utilizing the minimum available PTFE wall thickness tubing, a much greater efficiency in the system of the invention could be expected.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A flow-through vacuum degassing unit for degassing one or more liquids comprising:
   (a) a vacuum chamber adapted to be connected to a source for creating a vacuum in the chamber;
   (b) inlet and outlet connections for admitting and discharging liquid to be degassed;
   (c) one or more continuous tubes for conducting the liquid through the chamber, each such tube being connected between one of said inlet and one of said outlet connections and each such tube being formed in a predetermined, memoried configuration having an outer surface and being capable of self-supported containment in an unreinforced state in the vacuum chamber, such that the outer surface of such continuous tube is essentially totally exposed to the vacuum, each such tube being a thin-walled polymeric resin material permeable to pass dissolved atmospheric gases therethrough but liquid impermeable.

2. The apparatus of claim 1 wherein said inlet and outlet connections further comprise a plurality of inlet and outlet connections and wherein said one or more continuous tubes comprise a plurality of continuous tubes located within the vacuum chamber for simultaneously conducting a plurality of liquids in parallel through the chamber.

3. The apparatus of claim 2 wherein the tube has a wall thickness from about 0.013 mm to 0.04 mm and a nominal inside diameter of approximately 1.6 mm.

4. The apparatus of claim 1 wherein the thin-walled polymeric resin material is a fluorinated polymer.

5. The apparatus of claim 4 wherein the polymeric resin material is non-porous polytetrafluoroethylene (PTFE).

6. The apparatus of claim 5 wherein each tube has a wall thickness $\leq 0.04$ mm.

7. The apparatus of claim 5 wherein the thin-walled polymeric resin material of the one or more tubes has a thickness $\leq 0.04$ mm and is thermally formed by being wound about a form to produce a coil configuration, being heated while in the coil configuration on the form to a temperature of between 175° C. to 205° C. while at the same time being inflated to approximately 1.4 kg/cm$^2$ for a period of time followed by cooling in said coil configuration and inflated condition.

8. The apparatus of claim 7 wherein each tube has a wall thickness from about 0.013 mm to 0.04 mm and a nominal inside diameter of approximately 1.6 mm.

9. The apparatus of claim 5 wherein the tube has a wall thickness from about 0.013 mm to 0.04 mm and a nominal inside diameter of approximately 1.6 mm.

10. The apparatus of claim 4 wherein each tube has a wall thickness $\leq 0.04$ mm.

11. The apparatus of claim 1 wherein the memoried configuration is a self-supporting coil and further comprising guide means for guiding the location of the coil.

12. The apparatus of claim 11 wherein the tube has a wall thickness $\leq 0.04$ mm.

13. The apparatus of claim 1 wherein the memoried configuration is produced by thermal treatment.

14. The apparatus of claim 1 wherein the tube has a wall thickness from about 0.013 mm to 0.04 mm and a nominal inside diameter of approximately 1.6 mm.

15. The apparatus of claim 1 wherein the inlet and outlet connections contain no metal.

16. The apparatus of claim 1 wherein the inlet and outlet connections contain a double ended ferrule.

17. The apparatus of claim 1 wherein the vacuum chamber is configured entirely of non-metallic materials and wherein the inlet and outlet connections contain no metal.

18. A flow-through vacuum degassing unit for degassing one or more liquids comprising:
   (a) a vacuum chamber adapted to be connected to a source for creating a vacuum in the chamber;
   (b) inlet and outlet connections for admitting and discharging liquid to be degassed;
   (c) one or more continuous tubes for conducting the liquid through the chamber, each such tube being connected between one of said inlet and one of said outlet connections and each such tube having an outer surface being formed in a predetermined, memoried configuration that essentially exposes the entire outer surface to the vacuum chamber and being capable of self-supported containment in an unreinforced state in the vacuum chamber, each such tube being a thin-walled non-porous fluorinated polymer resin material having a wall thickness $\leq 0.04$ mm and permeable to pass dissolved atmospheric gases therethrough but liquid impermeable.

* * * * *